US005653767A

United States Patent [19]
Allen et al.

[11] Patent Number: 5,653,767
[45] Date of Patent: Aug. 5, 1997

[54] PROSTHETIC FOOT

[75] Inventors: Scott E. Allen, South Jordan; Phillip Ray Allen, Jr., Spanish Fork, both of Utah

[73] Assignee: Medonics, LLC, Salt Lake City, Utah

[21] Appl. No.: 571,362

[22] Filed: Dec. 12, 1995

Related U.S. Application Data

[60] Continuation-in-part of Ser. No. 232,946, Aug. 19, 1994, which is a division of Ser. No. 977,806, Nov. 17, 1992, Pat. No. 5,443,528.

[51] Int. Cl.$^6$ ........................................ A61F 2/66
[52] U.S. Cl. ................................. 623/52; 623/55
[58] Field of Search ....................... 623/47, 50–53, 623/54, 55

[56] References Cited

U.S. PATENT DOCUMENTS

| | | |
|---|---|---|
| 42,799 | 5/1864 | Shepard ................... 623/54 X |
| 428,839 | 5/1890 | Gault . |
| 563,247 | 7/1896 | Andrews . |
| 597,465 | 1/1898 | Hagen . |
| 942,521 | 12/1909 | Rowley . |
| 1,071,230 | 8/1913 | Hanger . |
| 1,289,580 | 12/1918 | Vincenti . |
| 1,319,471 | 10/1919 | Giebeler-Wanke . |
| 1,459,564 | 6/1923 | Tracy . |
| 2,036,830 | 4/1936 | Rowley . |
| 2,443,356 | 6/1948 | Mathis . |
| 2,470,480 | 5/1949 | Fogg . |
| 2,475,372 | 7/1949 | Catranis . |
| 2,475,373 | 7/1949 | Catranis . |
| 2,605,475 | 8/1952 | Burger et al. . |
| 2,619,652 | 12/1952 | Vesper . |
| 2,749,557 | 6/1956 | Riddle . |
| 3,551,914 | 1/1971 | Woodall . |
| 3,754,286 | 8/1973 | Ryan . |
| 3,920,610 | 11/1975 | Wagner . |
| 4,306,320 | 12/1981 | Delp . |
| 4,328,594 | 5/1982 | Campbell et al. . |
| 4,364,128 | 12/1982 | Mummert . |
| 4,446,580 | 5/1984 | Furuya et al. . |
| 4,506,395 | 3/1985 | Haüpt . |
| 4,547,913 | 10/1985 | Phillips ........................ 623/27 |
| 4,636,220 | 1/1987 | Ziegelmeyer ................ 623/53 |
| 4,650,492 | 3/1987 | Barkhordar et al. ......... 623/24 |
| 4,718,913 | 1/1988 | Voisin ........................... 623/49 |
| 4,721,510 | 1/1988 | Cooper et al. ................ 623/55 |
| 4,770,662 | 9/1988 | Giampapa ..................... 623/24 |
| 4,808,187 | 2/1989 | Patterson et al. ............. 623/25 |
| 4,822,363 | 4/1989 | Phillips ........................ 623/27 |
| 4,865,612 | 9/1989 | Arbogast et al. ............. 623/55 |
| 4,892,553 | 1/1990 | Prahl ............................ 623/55 |
| 4,959,073 | 9/1990 | Merlette ....................... 623/55 |
| 5,037,444 | 8/1991 | Phillips ........................ 623/55 |

(List continued on next page.)

FOREIGN PATENT DOCUMENTS

| | | |
|---|---|---|
| 583917 | 7/1924 | France . |
| 2 626 463 | 1/1988 | France . |
| 295807 | 12/1916 | Germany . |
| 325171 | 9/1920 | Germany . |
| 306313 | 2/1929 | United Kingdom ........... 623/53 |

OTHER PUBLICATIONS

"The Seattle Lightfoot", marketing brochure.
"The New Modular–III Flex–Foot and Flex–Walk II", marketing brochure.
"Carbon Copy System III", marketing brochure.

*Primary Examiner*—David H. Willse
*Attorney, Agent, or Firm*—Madson & Metcalf

[57] ABSTRACT

The prosthetic foot includes an extending forefoot and an extending heel which curve into arcing sections to be positioned in an overlapping and opposite fashion. A fastener securely fastens the forefoot and the heel to one another at a convergence of the arcing sections. The arcing sections define a receptacle for elements which limit the deflection of the forefoot and the heel. The preferred embodiment has a plurality of individual forefoot and heel members which readily accommodate uneven or angled terrain by individually flexing to conform to the terrain.

23 Claims, 6 Drawing Sheets

U.S. PATENT DOCUMENTS

| | | | |
|---|---|---|---|
| 5,066,305 | 11/1991 | Firth | 623/55 |
| 5,112,356 | 5/1992 | Harris et al. | 623/49 |
| 5,116,381 | 5/1992 | Palfray | 623/33 |
| 5,116,383 | 5/1992 | Shorter et al. | 623/49 |
| 5,139,525 | 8/1992 | Kristinsson | 623/55 |
| 5,246,463 | 9/1993 | Giampapa | 623/24 |
| 5,376,141 | 12/1994 | Phillips | 623/55 |

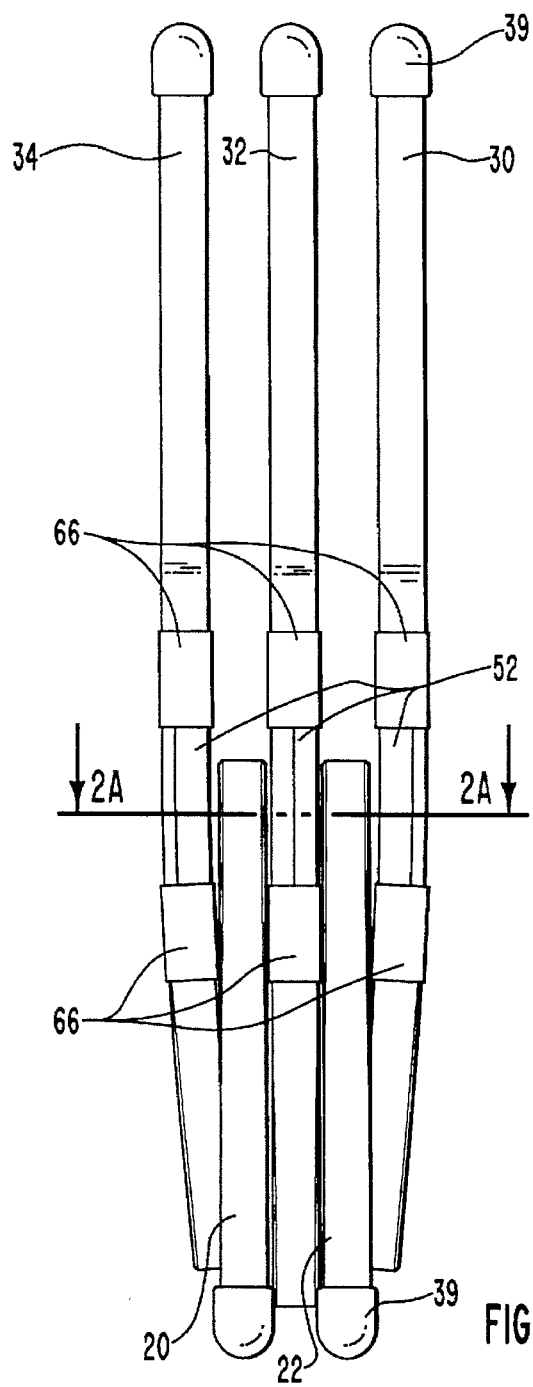
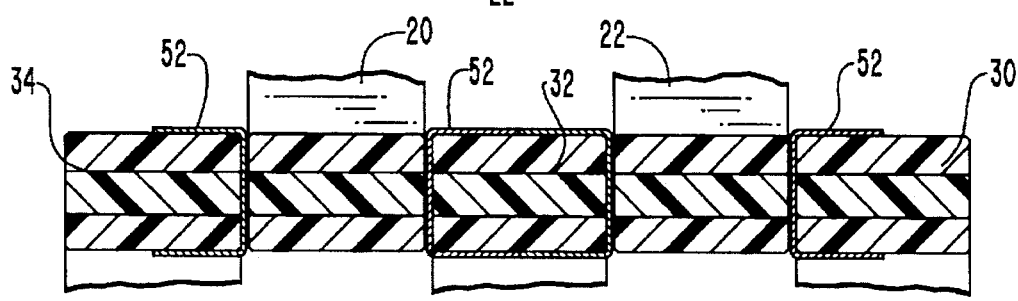
FIG. 2
FIG. 2A

PROSTHETIC FOOT

BACKGROUND OF INVENTION

A. Related Application

This application is a continuation-in-part of U.S. patent application Ser. No. 08/232,946, filed Aug. 19, 1994 and entitled "Prosthetic Foot" now pending, which is a divisional application of U.S. patent application Ser. No. 07/977, 806, filed Nov. 17, 1992 and entitled "Coil Spring Prosthetic Foot" which has now issued as U.S. Pat. No. 5,443,528. This application and patent are incorporated by reference.

B. The Field of the Invention

This invention relates to the field of prosthetic foot and leg devices, particularly those providing lateral and medial movement, shock absorption, and a smooth uninterrupted foot action to assist the prosthetic foot in approximating the response and performance of a natural foot.

C. The Background Art

Various prosthetic feet in the prior art have been designed with spring components intended to store energy when the foot is placed on the ground and to release it and provide a lift or thrust as the foot is removed from the ground again to aid in the patient's gait. Examples of this are Abrogast et al., U.S. Pat. No. 4,865,612 (Issue Date: Sep. 12, 1989) and Shorter et al. U.S. Pat. No. 5,116,383 (Issue Date: May 26, 1992) which are hereby incorporated by reference. Other prosthetic feet in the prior art have used an ankle joint intended to accommodate terrain and walking conditions. Example of this are Voisin, U.S. Pat. No. 4,718,933 (Issue Date: Jan. 12, 1988) and Delp, U.S. Pat. No. 4,306,320 (Issue Date: Dec. 22, 1981) which are hereby incorporated by reference. Poggi et al., U.S. Pat. No. 4,645,509 (Issue Date: Feb. 24, 1987), which is hereby incorporated by reference, disclosed a prosthetic foot which could accommodate uneven terrain by utilizing separate individual toe portions as part of a monolithic cantilever beam. Other prosthetic feet in the prior art have employed multiple springs, including multiple leaf springs, in an attempt to approximate the response and performance of a natural foot. Examples include Merlette, U.S. Pat. No. 4,959,073 (Issue Date: Sep. 25, 1990); Phillips, U.S. Pat. No. 4,547,913 (Issue Date: Oct. 22, 1985); Phillips, U.S. Pat. No. 4,822,363 (Issue Date: Apr. 18, 1989); and Phillips, U.S. Pat. No. 5,037,444 (Issue Date: Aug. 6, 1991), each of which is hereby incorporated by reference.

No prosthetic foot in the prior art has been completely successful in approximating the performance and response of a natural foot, however. Those prior art prosthetic feet which did not utilize a spring-loaded heel, such as Voisin and Delp, experienced a lag or deadness after the patient placed the heel on the ground and began to roll the foot forward during the gait cycle. This was due to the necessity of loading a spring in the toe section after the patient's weight had been placed on the ground. The response and feel of a natural foot cannot be achieved unless the spring(s) are loaded as the patient's weight is placed on the ground rather than after. Prior art prosthetic feet that utilized a spring-loaded heel which operated on a spring separate from a spring in the toe section, such as the Phillips patents and Merlette, effectively stored energy in the heel, but required a separate loading of a spring in the toe-section. As a result, the patient noticed a distinct and unnatural lag or hesitation in rolling the foot forward during the gait cycle, giving the foot an unnatural feel and possibly causing an uneven stride. Those prior art prosthetic feet which utilized a one-piece spring throughout the foot, such as Shorter et al., experienced a lag or deadness after the patient placed the heel on the ground and began to roll forward because the spring design was not suited to absorb and store sufficient energy in the heel and then transfer it to the toe section, thus requiring the toe section to be loaded after the patient's weight had been placed on the ground. Some prior art prosthetic feet, such as Phillips (U.S. Pat. No. 4,547,913) could accommodate torsional movement about the longitudinal axis of the shin portion, but the shape of the shin portion was designed for spring strength and breaking strength, not torsional movement, and the torsional stiffness of the shin section was not adjustable. Finally, prosthetic feet in the prior art lacked any effective means for absorbing and storing energy when vertical force is applied to the foot. Prior art prosthetic feet which utilized a plurality of springs, such as Phillips, tended to rock under vertical load as the load was distributed separately to the springs. Prior art prosthetic feet with a single spring member and a foam heel tended to absorb vertical load either in the spring member or in the foam heel, but not in both. Thus, the prior art exhibited a need for a prosthetic foot which approximates the performance and response of a natural foot by using a resilient heel section integrated with a resilient toe section such that the heel and toe interacted during the gait cycle to prevent lag or hesitation, a prosthetic foot that can accommodate angled or uneven terrain, a prosthetic foot capable of accommodating lateral and medial movement, a prosthetic foot capable of accommodating torsional movement about the longitudinal axis of the shin with means for adjusting torsional stiffness and a prosthetic foot capable of evenly absorbing and storing energy when vertical force is applied to the foot.

SUMMARY OF THE INVENTION

The present invention is directed to a novel prosthetic foot which approximates the smooth gait of a natural foot by storing and releasing energy in a heel and forefoot during a gait cycle. The invention substantially comprises an extending forefoot and an extending heel which curve into arcing sections to be positioned in an overlapping and opposite fashion. A fastener securely fastens the forefoot and heel to one another at a convergence of the arcing sections. The arcing sections define a receptacle which can accommodate means for limiting the deflection of heel and forefoot. The preferred embodiment of the invention has a plurality of individual forefoot and heel members which readily accommodate uneven or angled terrain without the use of an ankle joint by individually flexing to conform to the terrain. Lateral and medial movement is accommodated by the individual forefoot and heel members.

The invention provides a prosthetic foot which achieves a more natural gait without lag or hesitation. The invention provides a prosthetic foot with heel extension and a forefoot extension integrated so that there is a natural transition of flexibility in the gait cycle. The invention provides a prosthetic foot which has a plurality of forefoot and heel extensions which can accommodate uneven or angled terrain without the use of an ankle joint. The invention provides a prosthetic foot which utilizes a structure with two arcing sections having either single or a plurality of forefoot and heel extensions. The invention provides a prosthetic foot which can accommodate lateral and medial movement by use of forefoot and heel extensions. The invention provides a prosthetic foot which includes a mechanism for limiting the deflection of the arcing sections. The invention provides a prosthetic foot which has high flexibility strength. The invention provides a prosthetic foot which has high breaking strength. The invention provides a prosthetic foot which approximates the performance and response of a natural foot. Further advantages of the invention will become apparent to those skilled in the art.

BRIEF DESCRIPTION OF THE DRAWINGS

FIG. 2 is a bottom plan view of one embodiment of the invention.

FIG. 2A is a cut away sectional view of the overlapping heel extensions and forefoot extensions including the glide plates along line 2A—2A.

DETAILED DESCRIPTION OF THE PREFERRED EMBODIMENT

Figure 1:
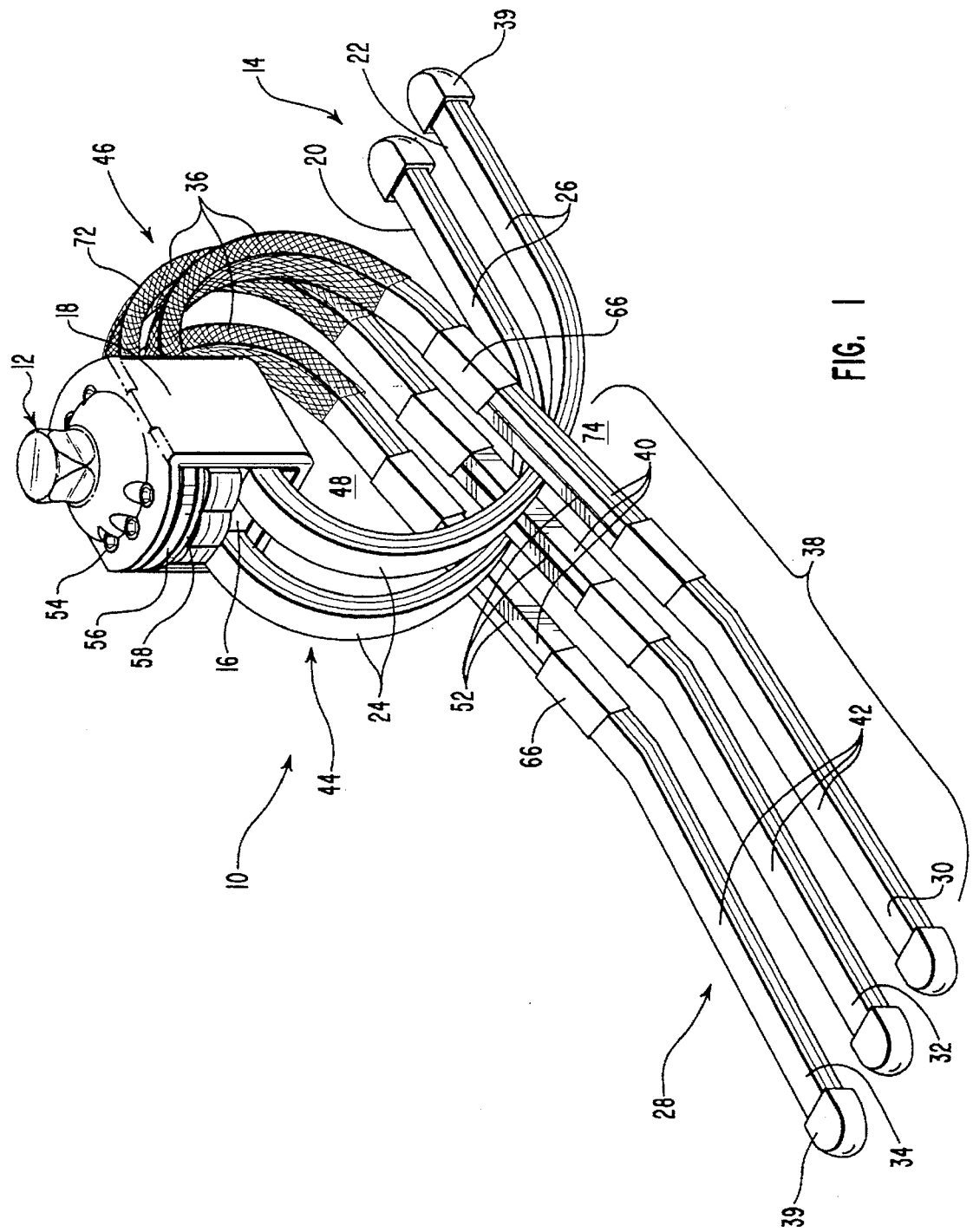
FIG. 1 is a perspective view of one embodiment of the invention with a pyramid connector.

Reference is now made to the figures wherein like parts are referred to by like numerals throughout. Referring to FIG. 1, a prosthetic foot 10 with a universal connector 12 for attachment to a shin section or ankle fixture is shown. The prosthetic foot 10 has a heel 14 which comprises a spacer 16 disposed within a fastener 18 and a medial heel extension 20 and a lateral heel extension 22. Each heel extension 20, 22 comprises an anterior arc section 24, and a heel section 26. The forefoot 28 comprises three forefoot extensions 30, 32, 34: lateral 30, mid 32, and medial 34. Each forefoot extension comprises a posterior arc section 36 and a toe section 38. The toe section 38 has a rear toe portion 40 and a fore toe portion 42. An anterior arc 44 is formed by the anterior arc sections 24 of the heel extensions 20, 22. Likewise, a posterior arc 46 is formed by the posterior arc sections 36 of the forefoot sections 30, 32, 34. The anterior arc 44 and posterior arc 46 form a receptacle 48 and together comprise the central and strongest part of the prosthetic foot 10. Heel sections 26 of the heel extensions 20, 22 extend in a posterior direction and toe sections 38 of the forefoot extensions 30, 32, 34 extend in an anterior direction from the anterior arc 44 and posterior arc 46, respectively. The receptacle 48 may accommodate an optional device for limiting deflection in the forefoot extension 30, 32, 34 such as an arc limiter 50 (not shown in FIG. 1) which will be discussed hereafter. Glide plates 52 are shown substantially covering the rear toe portions of each of the individual toe sections 38. Fore toe portions 42 are situated at an angle to rear toe portions 44 so that the fore toe portions 42 extend slightly upward when the foot 10 is resting on the ground. Each portion of the toe section 38 is chosen of a length to approximate not only the size and contour of a natural foot, but also the performance characteristics of a natural foot. The ends of each heel extension 20, 22 and each forefoot extension 30, 32, 34 are tipped with plastic caps 39 to soften the blunt edges of each extension.

Lateral and medial flexibility of the prosthetic foot 10 is provided by the individual sections of the forefoot extensions 30, 32, 34 and heel extensions 20, 22. Each individual forefoot extension 30, 32, 34 and heel extension 20, 22 permit lateral and medial movement of the foot 10 to accommodate uneven or angled terrain without the necessity of an ankle joint. The number of individual heel and forefoot extensions varies from one each to plural extensions, although a plurality is preferred. Alternatively, the invention could use a single forefoot extension and a single heel extension rather than a plurality of forefoot and heel extensions. In the preferred embodiment, there are three forefoot extensions 30, 32, 34 and two heel extensions 20, 22. The shape and joining of the various extensions comprise the foot 10 with anterior arc sections 24 forming an anterior arc 44, posterior arc sections 36 forming a posterior arc 46, and with both the anterior arc 44 and posterior arc 46 forming a receptacle 48 region. Heel extensions 20, 22 and forefoot extensions 30, 32, 34 overlap each other as they extend from the anterior arc section 24 and posterior arc section 36. The anterior arc 44 and posterior arc 46 also have the ability to absorb shock or energy as force is applied to the foot 10 at the universal connector 12.

The receptacle 48 may be a closed plane curve, and the points along the curve (i.e., along the anterior arcs 44 and posterior arc 46) may be equidistant from the center of a closed plane to form a circle or they may be of varying distances from the center to form other shapes. In the preferred embodiment, the receptacle 48 is formed by the anterior arc 44 and posterior arc 46 and as such lacks a continuous and uninterrupted interior surface but forms the general shape of an oval region.

The exact size and shape of the anterior arc 44 and posterior arc 46 depends on the size, weight and activity characteristics of the patient who is to wear the prosthetic foot 10. Varying size, shape, contour, strength, materials and other characteristics of the arc sections 24, 36 yields different flexibility characteristics and response abilities. Adjustment may be made to vary the flexibility and/or arc height in the anterior arc 44 and posterior arc 46. Each heel extension 20, 22, and forefoot extension 30, 32, 34 may be of a different strength and of varying thickness along their length to possess characteristics as similar as possible to a natural foot. This produces a differential in flexibility. Variation in lengths, widths, thicknesses and strength will be necessary depending upon the size, weight, and activity level of the patient.

In a preferred embodiment, the prosthetic foot 10 is composed of heel extensions 20, 22 and forefoot extensions 30, 32, 34 which overlap each other, form an arc sections 24, 36, and then fasten to each other. These extensions may be fastened to each other by the use of clamps, bolts, screws, chemical bonding such as adhesive or epoxy, welding or otherwise.

Figure 6:
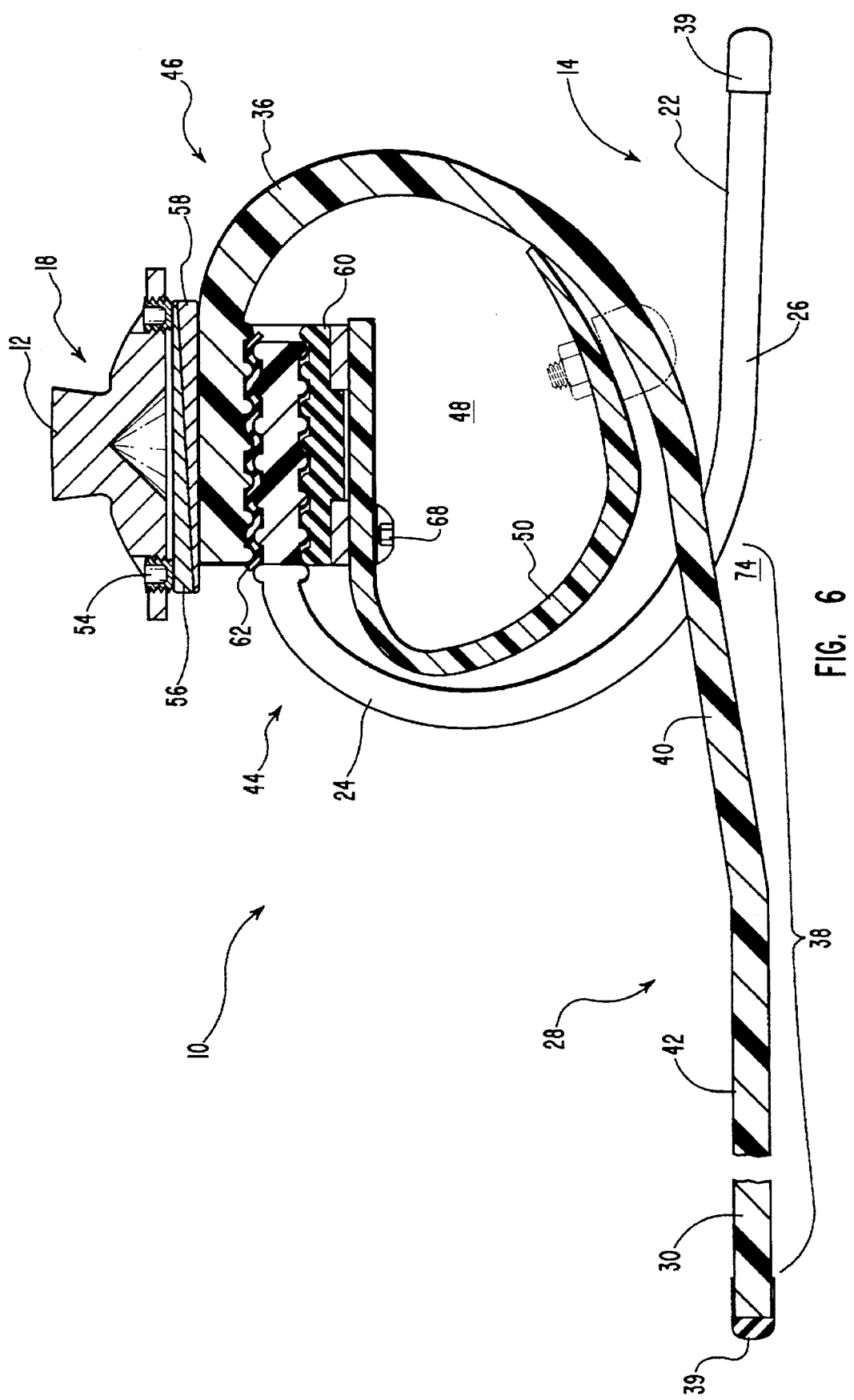
FIG. 6 is a side sectional view of one embodiment of the invention showing a bumper in phantom lines.

Referring now to FIG. 6, a fastener 18 is used which is a four walled housing device composed substantially of titanium. The fastener 18 receives the spacer 16, the ends of the heel extensions 20, 22, the ends of the forefoot extensions 30, 32, 34, and shims 56, 58, 60, 62 as will be described below. The fastener 18 acts to securely clamp the heel extensions 20, 22 with the forefoot extensions 30, 32, 34 where the heel extensions 20, 22 and forefoot extensions 30, 32, 34 converge, thereby joining the members to form the foot 10. The fastener 18 effectuates clamping by the use of six 6 mm stainless steel allen screws 54 that tighten from the top surface of the fastener 18 and engage a top shim 56 which is positioned below the top surface of the fastener 18. The top shim 56 is equipped with a nipple on its top surface to interface with a hole in the bottom of the top surface of the fastener 18. The top shim 56 is disposed above a bottom shim 58 with the interface between top shim 56 and bottom shim 58 being serrated to create an interlocking surface between the shims 56 and 58. Both the top shim 56 and bottom shim 58 are composed of a solid material such as stainless steel and have a greater thickness on one end than the other. Interfacing contact between the top shim 56 and bottom shim 58 is such that the thicker end of one opposes the thinner end of the other. The interlocking surface and positioning of the shims 56 and 58 prevents removal of either shim 56 or 58 by applied pressure to the thick ends. Removal of either shim 56 or 58 is accomplished by applying pressure to the thin ends of the respective shim.

The ends of each forefoot extension 30, 32, 34 lie below the bottom shim 58 and above the ends of each heel extension 20, 22. Each end of a heel extension 20, 22 lies in contact with one end of a forefoot extension 30, 32, 34 with the spacer 16 being disposed between the two heel extensions 20, 22. The spacer 16 is composed of the same material as are the forefoot extensions 30, 32, 34 and the heel extensions 20, 22. In the preferred embodiment, there are two heel extensions 20, 22 and three forefoot extensions 30, 32, 34. Thus, in order to accommodate all three forefoot extensions 30, 32, 34, the lateral forefoot extension 30 engages the lateral heel extension 22, the mid forefoot extension 32 engages the spacer 16 and the medial forefoot extension 34 engages the medial heel extension 20.

In order to further secure the ends of each forefoot extension 30, 32, 34 with the ends of each heel extension 20, 22, the ends of each forefoot extension 30, 32, 34 and heel extension 20, 22 as well as the spacer 16 are configured with corrugations or grips. The grips allow for an interlocking engagement between the extension ends and spacer 16 to increase the friction. Thus, the grips act to prevent any sliding and limit the surface displacement of the spacer 16 and extensions 20, 22, 30, 32, 34 with respect to one another.

A heel shim 60 is disposed below the ends of each heel extension 20, 22 and contacts with the bottom surface of the fastener 18. The heel shim 60 is preferably composed of a resilient material, such as rubber, and is configured with a nipple which fits into a hole on the top of the bottom surface of the fastener 18. Furthermore, the heel shim 60 is configured with corrugations or grips to engage the grips of the spacer 16 and the ends of the heel extensions 20, 22 to limit surface displacement.

If engagement of the ends of the forefoot extensions 30, 32, 34 with the heel extensions 20, 22 and spacer 16 appears slack, an additional flat shim 62 of resilient material, such as rubber, is inserted between the corrugated surfaces of the spacer 16, heel extensions 20, 22, and forefoot extensions 30, 32, 34. Placement of the additional flat shim 62 may be required if heel extensions 20, 22, or forefoot extensions 30, 32, 34 of different configuration or weight are used than those extensions originally placed in the fastener 18.

After proper placement in the fastener 18 of the spacer 16, the extensions 20, 22, 30, 32, 34, and shims 56, 58, 60 and 62, the allen screws 54 in the top surface of the fastener are tightened to an appropriate torque. This engages the screws 54 against the top shim 56, compresses the spacer 16 and extensions 20, 22, 30, 32, 34 in the fastener 18 together, and secures the position of the spacer 16, extensions 20, 22, 30, 32, 34, and shims 56, 58, 60 and 62 to create the foot 10.

Figure 4:
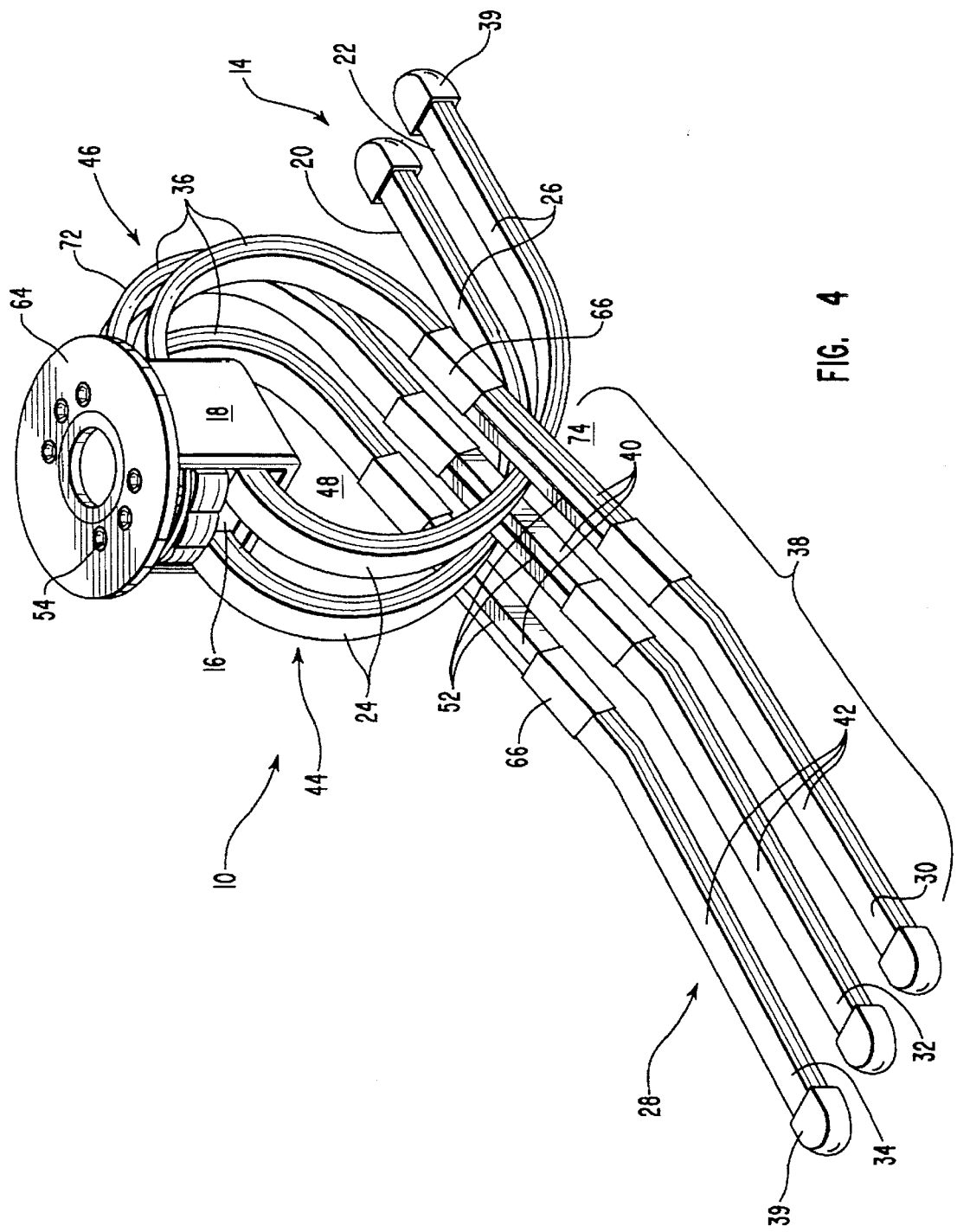
FIG. 4 is a perspective view of another embodiment of the invention showing a BK connector.

The fastener 18 further comprises a universal connector 12, being of a type commonly used in the art,. for attachment to a shin section or ankle joint. The preferred embodiment utilizes either a pyramid connector 12 (shown in FIG. 1) or a below-knee (BK) connector 64 (shown in FIG. 4), depending on the patient's needs. The pyramid connector 12 is commonly used for connection to an ankle fixture or shin and would make this embodiment of the invention suitable for a patient who had an amputation at some point above the ankle. The BK connector 64 is commonly used for a low-profile connection where the amputee is at a lower point on the leg and does not require a shin. The pyramid connector 12 and the BK connector 64 are well known in the prosthetic limb industry and those skilled in the art will appreciate their incorporation with preferred embodiments of the invention.

Referring to FIG. 2, the shape of the various heel extensions 20, 22 and forefoot extensions 30, 32, 34 which form the prosthetic foot 10 is shown. Medial heel extension 20 comprises heel section 26 which curves to become medial anterior arc section 36. Lateral heel extension 22 comprises heel section 26 which curves to become lateral anterior arc section 36. The forefoot extensions are similarly designed. Medial forefoot extension 34 comprises toe section 38 which curves to become medial posterior arc section 24. Mid forefoot extension 32 comprises toe section 38 which curves to become mid posterior arc section 24. Finally, lateral forefoot extension 30 comprises toe section 38 which curves to become lateral posterior arc section 24. At the point where the heel extensions 20, 22 and forefoot extensions 30, 32, 34 converge, they are secured together by the fastener 18 (not shown in FIG. 2).

A preferred embodiment also incorporates, as shown in FIG. 2, guide plates 52 disposed substantially at the rear toe portion 40 of the forefoot extensions 30, 32, 34 where the heel extensions 20, 22 overlap the forefoot extensions 30, 32, 34. The guide plates 52 act as sleeves to be inserted over the individual forefoot extensions 30, 32, 34. The purpose for each guide plate 52 is to prevent noise and wear resulting from the frictional contact of the heel extensions 20, 22 with the forefoot extensions 30, 32, 34. The guide plates 52 are preferably composed of a metallic material such as stainless steel. In this preferred embodiment, each guide plate 52 has a capturing end 66 disposed at each end of the guide plate 52 to limit the displacement of the guide plate 52 along the forefoot extension 30, 32, 34. The guide plate 52 should be immovable with finger pressure. As shown in FIG. 2, and more particularly in FIG. 2a, the guide plates 52 need only be disposed on the surface where contact with a heel extension 20, 22 is anticipated. Thus, lateral and medial forefoot extensions 30, 34 have guide plates 52 covering only the surfaces facing a heel extension 20, 22 whereas the mid forefoot extension 32 is encompassed with a guide plate 52. In alternative embodiments, the heel extensions 20, 22 may be covered with the guide plates 52 so long as wear between the forefoot extension 30, 32, 34 and heel extension 20, 22 is reduced.

Figure 3:
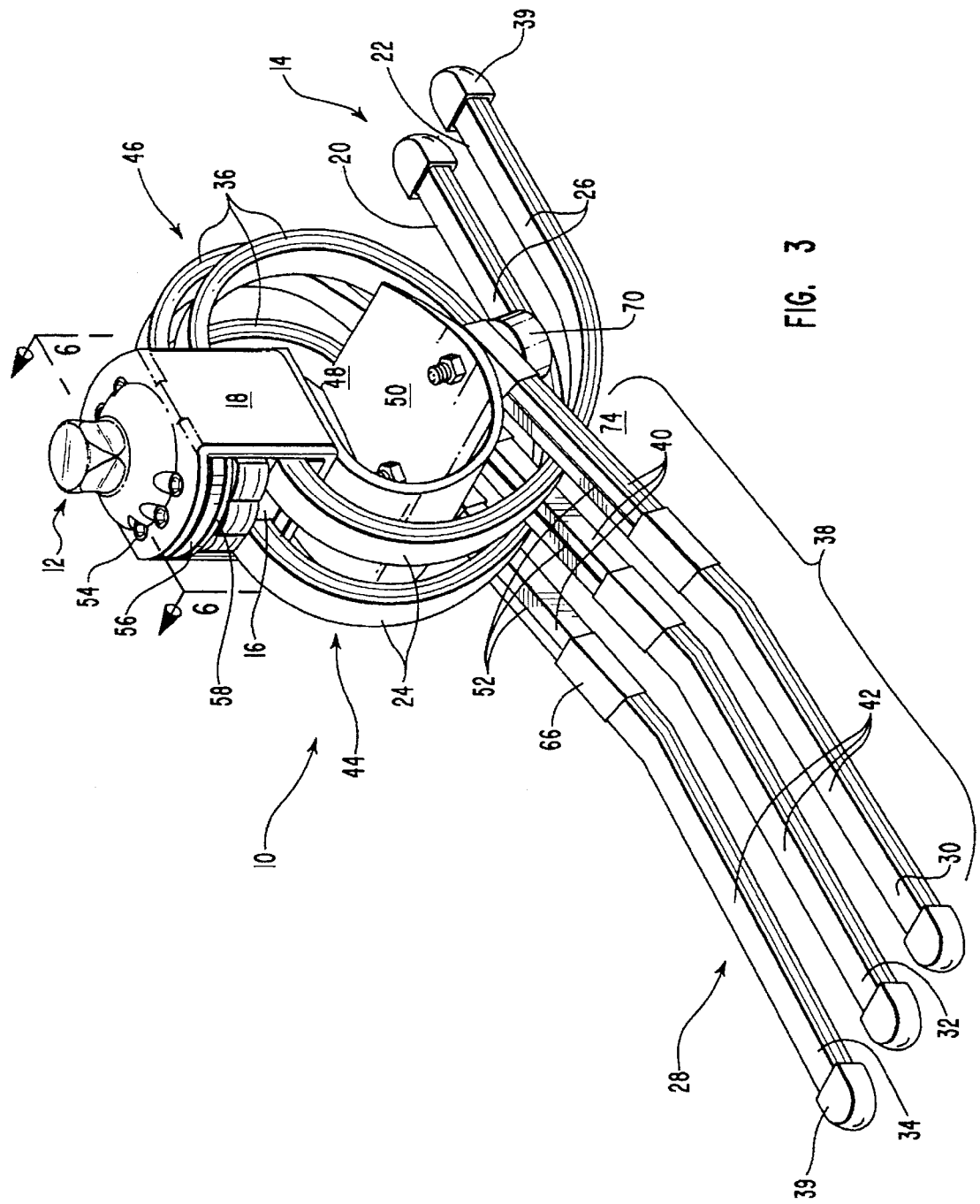
FIG. 3 is a perspective view of another embodiment of the invention showing an arc limiter disposed below the fastener.
Figure 5:
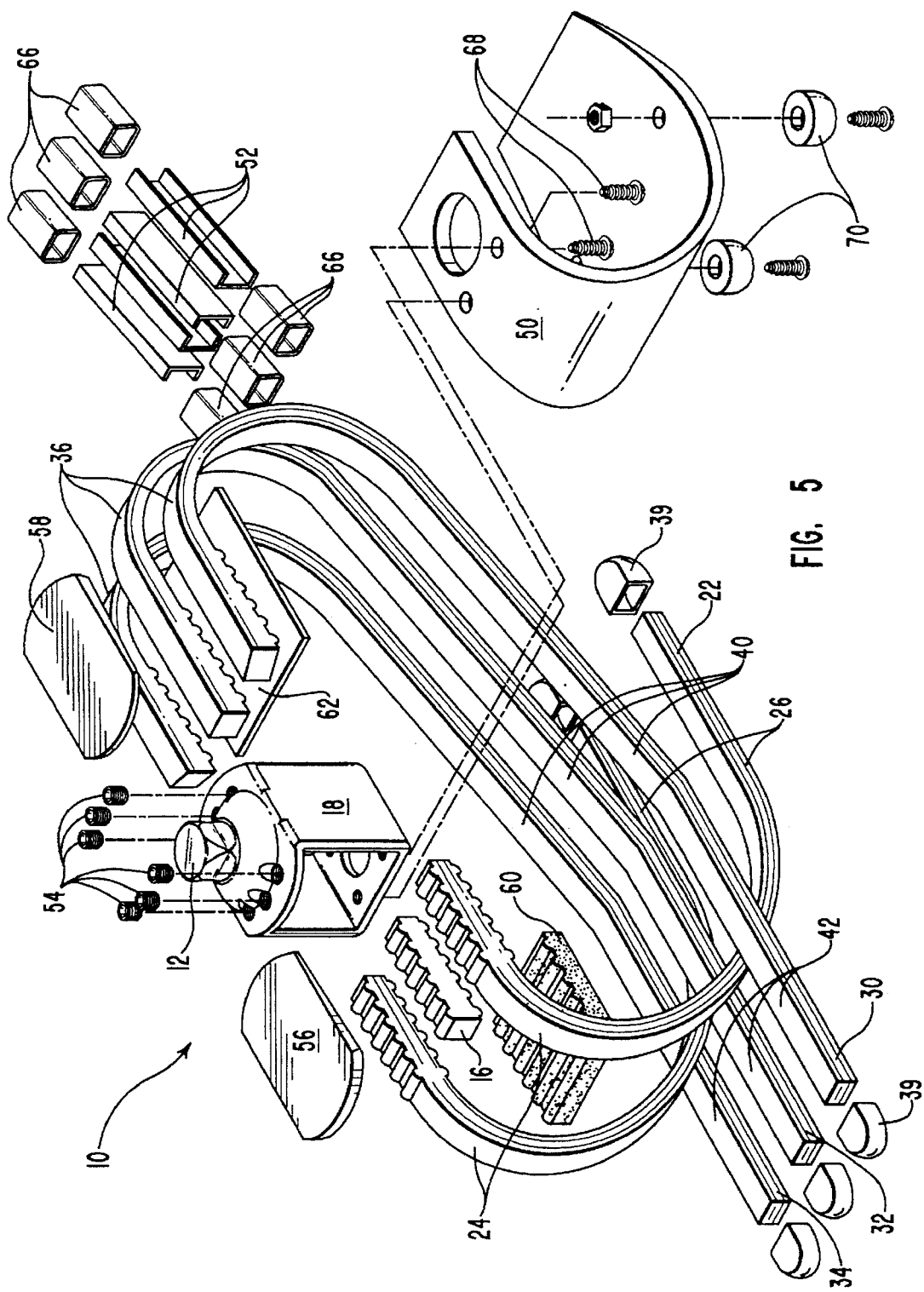
FIG. 5 is an exploded perspective view of the invention showing a preferred configuration of various components.

Referring to FIGS. 3, 5, and 6, an embodiment of the invention which includes an arc limiter 50 for limiting the deflection of the forefoot extension 30, 32, 34 is shown. Each forefoot extension 30, 32, 34 is placed under substantial stress during a toe-off phase of the gait cycle. During toe-off, each forefoot extension 30, 32, 34 is in contact with the ground and the heel is not. Accordingly, due to the stress, the forefoot extension 30, 32, 34 may experience excessive deflection and breaking may result. To limit the stress, an arc limiter 50, which is disposed in the receptacle 48 and subtends the fastener 18, is attached to the bottom surface of the fastener 18 by screws 68. The arc limiter 50 limits the deflection of the forefoot extensions 30, 32, 34 by engaging the forefoot extensions 30, 32, 34 when tension of a predetermined amount is applied during toe-off.

The arc limiter 50 is preferably composed of stainless steel and is configured in an arc to engage the forefoot extensions 30, 32, 34 when a predetermined amount of tensional force is applied. The arc limiter 50 is adjustable to vary the amount of deflection allowed in the forefoot extensions 30, 32, 34. The arc limiter 50 may be adjusted by varying its length, its curvature, or the resilience and/or thickness of the material composing the arc limiter 50.

An alternative embodiment of the invention is also shown in FIGS. 3, 5, and 6, wherein a bumper 70 is incorporated to limit deflection of the heel extensions 20, 22. During the heel strike portion of a gait cycle, the heel extensions 20, 22 contact the ground and the forefoot extensions 30, 32, 34 do not. Accordingly, the heel extensions 20, 22 are subject to tension and a certain amount of resulting deflection. Because the heel extensions 20, 22 are typically shorter than the forefoot extensions 30, 32, 34, the heel extensions 20, 22 are not normally subject to excessive deflection which will cause breaking. However, in the case of a patient who subjects the foot 10 to vigorous, athletic use, excessive deflection may result. In those situations, bumpers 70 may be disposed on the bottom of the arc limiter 50 extending downward toward the heel extensions 20, 22. In the preferred embodiment there are two bumpers 70, one corresponding to each heel extension 20, 22. Each bumper 70 comprises an attachment to the arc limiter 50, such as a screw, and has an end made of a resilient material such as rubber for contacting a heel extension 20, 22. Each bumper 70 limits the deflection of its corresponding heel extension 20, 22 by engaging the heel extension 20, 22 when a predetermined tension is applied during the heel strike phase of the gait cycle.

Various materials may be suitable for construction of the heel extensions 20, 22 and forefoot extensions 30, 32, 34 of the prosthetic foot 10. Graphite fiber, a graphite and fiberglass combination, spectra, kevlar or other fiber material impregnated with a resin such as epoxy or polyester resin are all suitable. Both Hercules and Newport Composites provide fabric pre-coated with a resin which may be used in foot assembly and then cured either by baking or chemically, as appropriate. In the preferred embodiment of the invention, graphite fiber fabric impregnated with epoxy resin is used, although other material may be equally suitable. This provides exceptionally high breaking and spring strength while being very light weight, durable, and long-lasting. Alternatively, the heel extensions 20, 22 and forefoot extensions 30, 32, 34 which comprise the foot 10 could be injection molded from delron or nylon with appropriately engineered strengths and thicknesses. Any materials or method of manufacture which provide adequate spring strength, stiffness, flexibility, resiliency, and bend without breaking or wearing quickly under constant use would be suitable. Furthermore, other materials such as plastics, metals, alloys, ceramics, etc., may be developed in the future which provide suitable or preferable characteristics for prosthetic foot construction.

Referring again to FIG. 1, an alternative embodiment incorporates a wrapping 72 which is disposed substantially along the posterior arc section 36 of each forefoot extension 30, 32, 34. The wrapping 72 is formed of a material composed of a graphite composite and is disposed in a braided fashion onto the posterior arc section 36. Although the composition of the forefoot extension 30, 32, 34 may vary, it is typically composed of laminated material in the preferred embodiment. Accordingly, the different laminated layers of the material are subject to different magnitudes of tensional force. The wrapping 72 acts to counter the different tensional forces by reinforcing and equalizing the forces throughout the posterior arc section 36. In alternative embodiments, the wrapping 72 may also be disposed on the anterior arc section 24 of the heel extensions 20, 22.

In alternative embodiments, the forefoot extensions 30, 32, 34 may be connected to each other via a strap or cord, as may the heel extensions 20, 22. When the foot 10 is in use, it is typically encased in a cosmetic foot shell resembling a natural foot. The foot shell can include bridges or grooves to keep each of the forefoot extensions 30, 32, 32 and heel extensions 20, 22 separate from the others and in alignment. The aforementioned strap, cord, bridges or grooves all serve as means for maintaining alignment and positioning of heel extensions 20, 22, and forefoot extensions 30, 32, 34.

Referring again to FIG. 6, a side sectional view of one embodiment of the invention is shown. The shape of the anterior arc sections 24 of the heel extensions 20, 22 and the posterior arc sections 36 of the forefoot extensions 30, 32, 34 form the receptacle 48 in a generally oblong or oval shape although an egg shape, circular shape, closed plane curve, arch shape or other shape to embody desired flexibility and natural foot performance characteristics would also be suitable. The invention may also be described as a plurality of arc sections 24, 36 oriented in an overlapping and opposite fashion. In FIG. 6, the anterior arc section 24 is oriented opposite and overlapping posterior arc section 36 to form a receptacle 48. Each heel extension 20, 22 employs a heel section 26 and an anterior arc section 24. Each forefoot extension 30, 32, 34 employs a toe section 38 and a posterior arc section 36. By using arc shaped sections of the heel extensions 20, 22 and forefoot extensions 30, 32, 34 and appropriate materials, resilient, flexible and durable arcs with natural foot-like responses are achieved. The orientation and overlap of the anterior arc 44 and posterior arc 46 form a prosthetic foot 10 when the extensions 20, 22, 30, 32, 34 are fastened together. An arch 74, positioned below the location of overlapping heel extensions 20, 22, and forefoot extensions 30, 32, 34 may also be included.

The anterior arc 44 and posterior arc 46 accommodate a means for adjusting the curvature of the arcs, the flexibility of the arcs, and arc height. In a preferred embodiment of the invention, the heel extensions 20, 22, and forefoot extensions 30, 32, 34, including their respective arc sections 24 and 36, are individually removable and replaceable in the aftermarket by the wearer or a service technician. The fastener 18 securing the heel extensions 20, 22, and forefoot extensions 30, 32, 34 can be released to allow removal of each individual extension. Once an extension is removed, another extension with an arc section with different arc degree, height, and/or strength and flexibility characteristics may be installed in the prosthetic foot 10. This allows aftermarket selection of heel extensions 20, 22, and forefoot extensions 30, 32, 34 of differential strengths to achieve lateral and medial adjustability of the prosthetic foot 10. In this manner, each heel extension 20, 22, and forefoot extension 30, 32, 34 may be of a different size and strength as appropriate for the particular patient. Through this selection of anterior and posterior arc sections 24, 36, a lateral and medial flexibility strength differential across heel extensions 20, 22 and across forefoot extensions 30, 32, 34 can be achieved. Worn or broken parts of the prosthetic foot 10 may be replaced in the same manner.

The invention seeks to incorporate the natural transition of flexibility found in the gait cycle of a natural foot. The gait cycle is the sequence of movements which a foot goes through from heel strike to mid foot to toe-off during normal walking, running, or jumping use. As the heel extension 20, 22 of the foot 10 are set onto the ground and weight applied, the heel sections 26 are compressed and store energy along their length and in the anterior arc sections 24. The heel section 26 along with the anterior arc section 24 comprise a means for absorbing and storing energy at heel strike during the gait cycle. At this point in the gait cycle, the toe section 38 of the foot 10 has not yet contacted the ground.

Mid foot (flat foot) in the gait cycle occurs as the foot 10 rolls from heel strike forward along the ground. The toe section 38 and the heel section 26 are in contact with the ground and are compressed or loaded under the weight of the patient's body. The arch 74 is similarly compressed. At this point, energy is stored by the toe section 38, the heel section 26, the arch 74, the anterior arc section 24, and the posterior arc section 36. As the foot rolls forward toward toe-off, energy is released from the heel section 26 and the arch 74 to provide smooth transition from heel strike to toe off. Because the foot 10 is composed of integrated arcs, no separate loading of different flexible members is required which would result in hesitation, lag or unevenness in the gait. Rather, the anterior arc 44 and posterior arc 46 act in concert to perform smooth and uninterrupted foot action through the gait cycle.

The foot 10 allows for a flexible response when the patient applies force to the universal connector 12 directly, such as when landing on the ground after jumping vertically. Toe sections 38, heel sections 26, anterior arc sections 24, posterior arc sections 36, and arch 74 are compressed and loaded as the patient's weight is applied to the foot 10. The arch 74 in conjunction with the toe sections 38, heel sections 26, and arc sections 24 and 36 serve as means for absorbing and storing energy when force is applied to the universal connector 12.

At toe-off in the gait cycle, the heel section 26 is no longer in contact with the ground. The heel section 26, along with the anterior arc section 24, has released the previously stored energy in making the transition from the heel strike stage of the gait cycle to the toe-off stage. As the foot 10 continues to roll forward and lose contact with the ground, energy stored in the posterior arc section 36 during mid foot is released and transferred into the toe section 38. As the foot 10 completes the gait cycle, fore toe portions 42 are the last portion of the foot 10 to be in contact with the ground, and through the toe sections 38 and constituent fore toe portions 42, energy transferred to the toe sections 38 is released to provide a gait-enhancing propelling force such as a bounce or a thrust on the foot 10 to aid in achieving a natural gait. This is in contrast with the inert feel of a non-spring loaded foot as it completes the gait cycle. The toe sections 38 in conjunction with the posterior arc sections 36 serves as a means for propelling the foot 10 forward during toe-off in the gait cycle.

The toe sections 38 and heel sections 26 have the ability to separately conform to and accommodate uneven or angled terrain without the use of an ankle joint. Each forefoot extension 30, 32, 34 and each heel extension 20, 22 is separately loaded according to the demands of the terrain and angle of the foot 10 with the ground. Energy is stored in the anterior arc 44 and posterior arc 46 according to the angle, terrain, and load applied. In this manner, lateral and medial movement is accommodated by the invention and the need for a jointed ankle portion of the prosthetic foot is eliminated. In this way, the response and performance of a natural foot are approximated.

The prosthetic foot 10 must be made with a flexible strength appropriate for the weight and activity level of the patient who is to wear and use it. Both the breaking strength and the spring strength of the foot may be engineered through proper selection of materials and a determination of the thickness of materials to be used in various portions of the foot. Phillips, U.S. Pat. No. 5,037,444 (Issue Date Aug. 6, 1991), which is hereby incorporated by reference, discloses a method for determining appropriate ply thickness of a prosthetic foot constructed from epoxy-impregnated graphite laminate. It should be noted that the graphite fiber material used to construct the preferred embodiment of the prosthetic foot has strength only along one axis and must therefore be laminated in some type of cross-hatched pattern to give strength from various directions. Merlette, U.S. Pat. No. 4,959,073 (Issue Date: Sep. 25, 1970), which is hereby incorporated by reference, describes methods for doing this. Foot length and width are chosen depending upon desired foot size. The number of forefoot and heel extensions should be selected to provide the performance characteristics sought by the invention, but not be so numerous and hence so thin as to lack strength and durability. As stated previously, two heel extensions and three forefoot extensions 30, 32, 34 are used in the preferred embodiment of the invention.

The invention is a prosthetic foot 10 which approximates the smooth gait of a natural foot by storing and releasing energy in the heel extensions 20, 22 and forefoot extensions 30, 32, 34 during the gait cycle. The release of stored energy in the extensions during the gait cycle provides a propelling force which gives a smoother gait. The invention eliminates any deadness or hesitation when the heel is placed on the ground and any lag or hesitation during foot roll-forward because of the interaction of the arc sections 24, 36 and the protruding members forming heel section 26 and toe section 38. The preferred embodiment of the invention has a plurality of heel extensions 20, 22, and forefoot extensions 30, 32, 34 which readily accommodate uneven or angled terrain. Another embodiment of the invention has single forefoot extension and a single heel extension which exhibit the same performance characteristics as the preferred embodiment but also easily accommodate uneven terrain. The preferred embodiment of the invention also accommodates angled or uneven terrain without the use of an ankle joint by using multiple forefoot and heel extensions which can individually flex to conform to the terrain. Lateral and medial movement is accommodated by the individual heel extensions 20, 22, and forefoot extensions 30, 32, 34. Each of the heel extensions 20, 22, and forefoot extensions 30, 32, 34 curves into arc sections to form an anterior arc 44 and a posterior arc 46. The anterior arc 44 and posterior arc 46 define a receptacle 48 which can accommodate a means for adjusting spring stiffness and arch height, and/or limit the deflection of heel and forefoot extensions. High flexibility strength and breaking strength are achieved in the preferred embodiment by the use of laminated graphite composite material impregnated with epoxy resin to construct the prosthetic foot. The prosthetic foot enables a patient to walk, run, play tennis, racquetball, and basketball and engage in other sports and vigorous activities with substantially the same mobility as an individual with a natural foot.

What is claimed and desired to be secured by United States Letters Patent is:

1. A prosthetic foot for attachment to a shin section or to an ankle fixture comprising:

a heel extension extending in a posterior direction;

a forefoot extension, distinct from said heel extension, extending in an anterior direction; and a fastener to secure said heel extension and said forefoot extension together such that a portion of said heel extension forms an arc anterior to said fastener and a portion of said forefoot extension forms an arc posterior to said fastener whereby said heel extension and said forefoot extension are oriented in an overlapping and opposite fashion, said fastener is substantially constructed of titanium.

2. A prosthetic foot device as defined in claim 1 wherein said fastener comprises a pyramid connector.

3. A prosthetic foot device as defined in claim 1 wherein said fastener comprises a below-knee connector.

4. A prosthetic foot device as defined in claim 1 wherein an arc limiter subtends said fastener and limits the deflection of said forefoot extension by engaging said forefoot extension if said forefoot extension is under a predetermined tension during the toe-off.

5. The prosthetic foot as defined in claim 4 wherein said arc limiter further comprises a bumper, said bumper limits the deflection of said heel extension by engaging said heel extension if said heel extension is under a predetermined tension during heel strike.

6. The prosthetic foot as defined in claim 4 wherein said arc limiter is adjustable to vary the amount of deflection allowed by said forefoot extension.

7. The prosthetic foot as defined in claim 6 wherein said arc limiter is adjusted by varying the length of said arc limiter.

8. The prosthetic foot as defined in claim 6 wherein said arc limiter is adjusted by varying the curvature of said arc limiter.

9. The prosthetic foot as defined in claim 6 wherein said arc limiter is adjusted by varying the resilience of said arc limiter.

10. The prosthetic foot as defined in claim 6 wherein said arc limiter is adjusted by varying the thickness of said arc limiter.

11. A prosthetic foot for attachment to a shin section or to an ankle fixture comprising:

a heel extending in a posterior direction, said heel comprises at least two heel extensions and a spacer;

a forefoot extension, separate from said heel, extending in an anterior direction; and a fastener to secure said heel and said forefoot extension together such that a portion of said heel forms an arc anterior to said fastener and a portion of said forefoot extension forms an arc posterior to said fastener whereby said heel and said forefoot extension are oriented in an overlapping and opposite fashion, said heel extensions being secured by said fastener such that said spacer is disposed between the two heel extensions.

12. A prosthetic foot as defined in claim 11 further comprising at least one shim disposed to engage said fastener in order to assist in securing said heel and said forefoot extension together.

13. A prosthetic foot as defined in claim 11 wherein each of heel extension ends proximate said fastener, forefoot extension ends proximate said fastener, and said spacer are configured with grips such that when engaged together the grips limit surface displacement relative to each other.

14. A prosthetic foot as defined in claim 11 further comprising a wrapping disposed substantially along the arc of said forefoot extension posterior to said fastener.

15. A prosthetic foot for attachment to a shin section or ankle fixture comprising:

a heel extension extending in a posterior direction;

a forefoot extension, distinct from said heel extension, extending in an anterior direction;

a fastener to secure said heel extension and said forefoot extension together such that a portion of said heel extension forms an arc anterior to said fastener and a portion of said forefoot extension forms an arc posterior to said fastener whereby said heel extension and said forefoot extension are oriented in an overlapping and opposite fashion; and an arc limiter which subtends said fastener and limits the deflection of said forefoot extension by engaging said forefoot extension if said forefoot extension is under a predetermined tension during toe-off.

16. The prosthetic foot as defined in claim 15 wherein said arc limiter comprises a bumper which limits the deflection of said heel extension by engaging said heel extension if said heel extension is under a predetermined tension during heel strike.

17. The prosthetic foot as defined in claim 15 wherein said arc limiter is adjustable to vary the amount of deflection allowed by said forefoot extension.

18. The prosthetic foot as defined in claim 17 wherein said arc limiter is adjusted by varying the length of said arc limiter.

19. The prosthetic foot as defined in claim 17 wherein said arc limiter is adjusted by varying the curvature of said arc limiter.

20. The prosthetic foot as defined in claim 17 wherein said arc limiter is adjusted by varying the resilience of said arc limiter.

21. The prosthetic foot as defined in claim 17 wherein said arc limiter is adjusted by varying the thickness of said arc limiter.

22. A prosthetic foot for attachment to a shin section or to an ankle fixture comprising:

a heel extension extending in a posterior direction;

a forefoot extension, distinct from said heel extension, extending in an anterior direction;

a fastener to secure said heel extension and said forefoot extension together such that a portion of said heel extension forms an arc anterior to said fastener and a portion of said forefoot extension forms an arc posterior to said fastener whereby said heel extension and said forefoot extension are oriented in an overlapping and opposite fashion; and a guide plate, disposed substantially at a rear toe portion of said forefoot extension where said forefoot extension overlaps said heel extension.

23. The prosthetic foot as defined in claim 22 wherein said guide plate has a capturing end disposed on each end of said guide plate to limit the displacement of said guide plate along said forefoot extension.

* * * * *